(12) United States Patent
von Locquenghien et al.

(10) Patent No.: US 6,353,134 B1
(45) Date of Patent: Mar. 5, 2002

(54) DIUREIDES AND THEIR USE

(75) Inventors: Klaus Horchler von Locquenghien, Limburgerhof; Klaus Erhardt, Leimen; Wolfgang Weigelt, Dudenhofen; Jürgen Dressel, Neuhofen; Alexander Wissemeier, Speyer; Frank Boerner; Gerhard Kossmehl, both of Berlin, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/515,647

(22) Filed: Feb. 29, 2000

(30) Foreign Application Priority Data

Mar. 3, 1999 (DE) ......................... 199 09 334
Dec. 2, 1999 (DE) ......................... 199 58 030

(51) Int. Cl.$^7$ ............................ C07C 275/00
(52) U.S. Cl. .......................... 564/44; 564/45
(58) Field of Search ............... 564/38, 39, 44, 564/45; 562/30, 37, 39

(56) References Cited

U.S. PATENT DOCUMENTS

| 2,090,594 A |   | 8/1937  | Jacobson ............... 260/33 |
| 2,615,000 A | * | 10/1952 | Bradley                        |
| 3,459,529 A |   | 8/1969  | Wiesboeck ............... 71/28 |
| 3,555,081 A | * | 1/1971  | Zirner et al.                  |
| 4,044,045 A | * | 8/1977  | Perkow et al.                  |
| 4,918,122 A |   | 4/1990  | Dellar et al. ........... 525/95 |
| 5,292,937 A |   | 3/1994  | Manning et al. .......... 562/457 |

FOREIGN PATENT DOCUMENTS

| DE | 32 41 445    | 5/1983  |
| WO | WO 87/05781  | 10/1987 |
| WO | WO 87/05897  | 10/1987 |
| WO | WO 97/05084  | 2/1997  |

OTHER PUBLICATIONS

Chem. Ber. 1913, 46, pp. 1404–1417.
J. Prakt. Chem. 1874, (2) 9, pp. 300–303.
Chem. Zentralbl. 1936, 107 (I) pp. 1218–1219.
Ullmann's Encyclopedia of Industrial Chemistry, vol. A10 (1987) pp. 398–401.

* cited by examiner

Primary Examiner—Jean F. Vollano
(74) Attorney, Agent, or Firm—Keil & Weinkauf

(57) ABSTRACT

The present invention relates to the use of diureides of dicarboxylic acids of the formula I

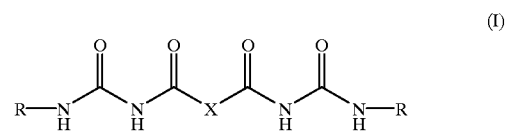

(I)

in which

R is hydrogen or $SO_2OM^\oplus$,

M is lithium, sodium, potassium, cesium, ammonium, copper, silver, 0.5 iron, 0.5 calcium, 0.5 magnesium, 0.5 manganese, 0.5 zinc or 0.5 cobalt and X is a saturated or monounsaturated, straight-chain or branched $C_1$-to $C_8$-alkyl which may be interrupted by oxygen or NH and which may have attached to it $C_1$-to $C_4$-alkoxy, hydroxyl and/or amino groups, as slow-release fertilizers and to novel diureides of the formula Ia

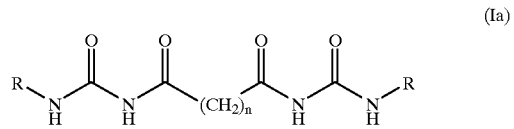

(Ia)

in which

R is $SO_2OM^\oplus$

M is lithium, sodium, potassium, cesium, ammonium, copper, silver, 0.5 iron, 0.5 calcium, 0.5 magnesium, 0.5 manganese, 0.5 zinc or 0.5 cobalt and n is 1,2,3 or 4, and a process for their preparation.

6 Claims, No Drawings

DIUREIDES AND THEIR USE

The present invention relates to fertilizers such as nitrogen fertilizers, in particular to known diureides and to novel diureides, to a process for their preparation, and to their use as slow-release fertilizers in agriculture and horticulture.

DD-A-264 372 and WO-A-87/05781 disclose similar malonic acid derivatives for delaying plant growth, and WO-A-87/05897 discloses similar malonic acid derivatives for increasing the yield. The compounds described therein are employed only at relatively low application rates, and their action is based on their property as growth regulators of reducing plant growth.

Chem. Ber. 1913, 46, page 1408 discloses oxalic acid diureide (R=M; X=single bond), EP-A-254 683 malonic acid diureide (R=H, X=CH$_2$), J. Prakt. Chem. 1874, (2) 9, page 301 succinic acid diureide (R=H, X=CH$_2$CH$_2$), US-A-2,090,594 glutaric acid diureide (R=H, X=CH$_2$CH$_2$CH$_2$), and Chem. Zentralbl. 1936, 107 (I), page 1218 fumaric acid diureide (R=H, X=CH=CH).

These compounds per se, and their synthesis, are known; their suitability and use as fertilizer, however, is novel.

It is an object of the present invention to find chemical compounds which are suitable as slow-release fertilizers and which are superior to the known substances with regard to their plant tolerance and duration of action. Furthermore intended was the possibility that the slow-release fertilizers comprise a plurality of plant nutrients, which they liberate in a delayed fashion.

We have found that this object is achieved by the use of diureides of dicarboxylic acids of the formula I

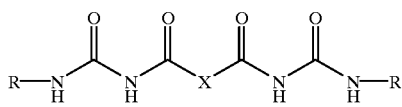

(I)

in which
R is hydrogen or SO$_2$O$^\ominus$M$^\oplus$,
M$^\oplus$ is lithium, sodium, potassium, cesium, ammonium, copper, silver, 0.5 iron, 0.5 calcium, 0.5 magnesium, 0.5 manganese, 0.5 zinc or 0.5 cobalt and
X is a saturated or monounsaturated, straight-chain or branched C$_1$- to C$_8$-alkyl which may be interrupted by oxygen or NH and which may have attached to it C$_1$- to C$_4$-alkoxy, hydroxyl and/or amino groups,
as slow-release fertilizers, novel diureides of the formula Ia

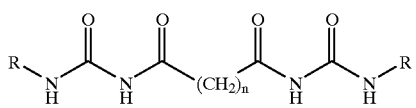

(Ia)

in which
R is SO$_2$O$^\ominus$M$^\oplus$,
M$^\oplus$ is lithium, sodium, potassium, cesium, ammonium, copper, silver, 0.5 iron, 0.5 calcium, 0.5 magnesium, 0.5 manganese, 0.5 zinc or 0.5 cobalt and
n is 1, 2, 3 or 4,
and a process for their preparation.

The compounds (Ia) of the invention can be prepared as follows:

Chlorosulfonyl isocyanate can be added to malonic diamide in a suitable solvent at a temperature of (−20) to +190° C., preferably (−15) to +50° C., especially preferably (−10) to 0° C. The resulting mixture can be poured onto ice, and an M$^\oplus$$_2$ carbonate solution, i.e., M$_2$CO$_3$, where M is equivalent to M$^\oplus$ as defined above, preferably a concentrated aqueous M$^\oplus$$_2$ carbonate (M$_2$CO$_3$) solution can subsequently be added at a temperature of (−10) to +50° C., preferably 0 to 30° C., especially preferably at room temperature (18 to 28° C.).

Suitable solvents which can be used are customary aprotic solvents, for example ethers such as diethyl ether, methyl tert-butyl ether or aromatic hydrocarbons such as benzene, toluene and xylenes, or nitriles such as acetonitrile and propionitrile, or ketones such as acetone, ethyl methyl ketone and diethyl ketone, esters such as methyl formate, ethyl formate, methyl acetate and ethyl acetate, sulfoxides such as dimethyl sulfoxide or formamides such as dimethylformamide, ethylmethylformamide and diethylformamide, or mixtures of these; aprotic solvents which are miscible with water are preferred, and acetonitrile, acetone, methyl acetate and dimethylformamide are especially preferred.

The preparation can be continuous or batchwise.

The compounds are surprisingly sparingly soluble in water and are therefore suitable as a source for slowly released plant nutrients. In the soil, they are subjected to slow mineralization (see below), where all the nutrients contained are gradually made available to the plant. In contrast to the above-described customary slow-release fertilizers, these nutrients are, in the case of the compounds of the invention, not only nitrogen, but also sulfur and (depending on the counterion M$^\oplus$) potassium, calcium, magnesium, iron, copper, zinc or manganese. What makes the compounds particularly interesting is their potential use as a combined nutrient source with slow-release properties for main nutrients such as N and K, secondary nutrients such as sulfur, magnesium and calcium and trace elements such as iron, copper, manganese and zinc.

The novel diureides I of the invention can be employed in relatively high quantities per hectare and result in improved yields owing to increased plant growth. The plant nutrients which the substances comprise gradually become available to the plant and therefore act as slow-release fertilizers.

Slow-release fertilizers have many advantages over conventional mineral or organic fertilizers. They permit the nutrient supply to be tailored better to the plant's requirements and therefore improve nutrient utilization. This leads to lower nutrient losses, thus reducing pollution and increasing fertilizer efficiency. They also permit savings to be made on passes and inputs and thus on agronomical costs.

A slow-release action of fertilizers can be achieved by various routes. One possibility is to provide granular fertilizers which are readily soluble in water with a coating which is insoluble in water. The nutrients are liberated from such coated fertilizers in a delayed manner since the nutrients must first diffuse through the coat before they can be absorbed by the roots. Another possibility is to apply the nutrients in the form of chemical compounds in which they are initially not available to the plants. It is only after an earlier liberation step, for example a chemical hydrolysis, an enzymatic cleavage and/or a microbial conversion, has taken place that the nutrients exist in a form which can be utilized by the plants. The invention described herein relates to fertilizers of this second group, i.e. the chemical slow-release fertilizers. Examples of such chemical slow-release fertilizers are urea/aldehyde condensates such as Isodur (DE-A-32 41 445) or Ureaform (WO-A-97/05084).

The compounds I of the invention can be employed as slow-release fertilizers alone or as mixtures or in combination with other customary fertilizers or additions. For example, they can be formulated together with customary potash fertilizers (K fertilizers) such as potassium chloride, potassium sulfate and potassium nitrate, nitrogen fertilizers (N fertilizers) such as nitrochalk, ammonium sulfate, ammonium nitrate, ammonium nitrate sulfate and urea, nitrogen/phosphorus fertilizers (NP fertilizers) such as ammonium phosphates, nitrogen/potash fertilizers (NK fertilizers) such as potassium ammonium sulfate, phosphorus/potash fertilizers (PK fertilizers) such as potassium phosphate or nitrogen/phosphorus/potash fertilizers (NPK fertilizers) such as potassium ammonium phosphate, all of which may have a slow-release action or not.

In addition to the abovementioned main constituents, a fertilizer of the invention may additionally comprise secondary nutrients such as calcium, sulfur and/or magnesium and trace elements such as boron, iron, manganese, copper, zinc and/or molybdenum in minor amounts, i.e. usually in amounts of 0.5 to 5% by weight, and other additives such as crop protection agents, for example insecticides, herbicides or fungicides, growth regulators or nitrification inhibitors.

For use, they can be brought to a desired particle size in the known manner, for example by granulation or compacting. Fertilizers thus formulated generally have a maximum mean particle diameter of 0.5 to 10 mm, preferably 0.7 to 5 mm. Their apparent weight is usually 0.5 to 1.3 kg/l.

The fertilizers according to the invention are usually applied to agricultural and horticultural areas by the generally known methods (cf. Ullmann's Encyclopedia of Industrial Chemistry, 5th edition 1987, Volume A 10, pages 398 to 401) or admixed into pot or container crops or growing media. Since they are well tolerated by plants, the granule mixtures of the invention are not only suitable for fertilizing methods in which the fertilizer is fairly uniformly applied to the area under cultivation, but also for the directed deposition in the vicinity of the plant root. The application rates are generally between 1 and 5000 kg/ha, especially advantageously between 20 and 1800 kg/ha.

In principle, the fertilizers of the invention can be employed in all sectors of crop production, such as agriculture and horticulture, mainly fruit and vegetable production. Crops whose growth can additionally be promoted in an efficient manner with the fertilizer of the invention are, for example, corn, cotton, sweet potatoes, potatoes, alfafa, wheat, rye, rice, barley, oats, panic grasses, dry beans, soya beans, sugar beet, sunflowers, tobacco, hops, tomatoes, canola, dehiscent fruit, citrus fruit, tea, coffee, olives, pineapples, cacao, bananas, sugar cane, oil palms, herbaceous outdoor plants, woody shrubs, turf grasses, ornamentals, evergreen plants, trees, flowers and the like.

The fertilizers of the invention are distinguished by the fact that they allow agricultural and horticultural areas to be utilized intensively in a particularly economical manner, largely avoiding pollution of the environment.

For an optimal growth promotion of the plants, it is usually sufficient to apply the fertilizers of the invention to the area under cultivation once per growth period (preferably at the beginning), since the course of the plants' nutrient requirements and the course of liberation of the fertilizer active substances are largely matched.

In the formulae I and Ia, the radicals R, R', X and the index n have the following meanings:

R is hydrogen

R,R' are $SO_2O^{\ominus}M^{\oplus}$, $M^{\oplus}$ is lithium, sodium, potassium, cesium, ammonium, copper, silver, 0.5 iron, 0.5 calcium, 0.5 magnesium, 0.5 manganese, 0.5 zinc or 0.5 cobalt, preferably sodium, potassium, ammonium, 0.5 iron, 0.5 manganese, 0.5 magnesium or 0.5 zinc, especially preferably sodium, potassium or 0.5 magnesium, X is a saturated or monounsaturated, straight-chain or branched $C_1$- to $C_8$-alkyl, preferably $C_1$- to $C_5$-alkyl, especially preferably methyl, ethyl, n-propyl, isopropyl, n-butyl, isobutyl, sec-butyl and tert-butyl, which may be interrupted by oxygen or NH and which may have attached to it $C_1$- to $C_4$-alkoxy, preferably methoxy or ethoxy, especially preferably methoxy, hydroxyl and/or amino groups, n is 1, 2, 3 and 4, preferably 1, 2 and 3, especially preferably 1 and 2.

USE EXAMPLE

The invention is illustrated by the examples which follow.

To demonstrate the action of these substances, extensive crop production experiments were carried out. To this end, experiments were set up in Mitscherlich containers with ryegrass as test crop, and the grass was cut at regular intervals, and its dry matter was determined and its nitrogen content was analyzed. Also, the plants were assessed prior to each cut and examined for damage. The nitrogen application of 2.4 g of N per container, which corresponded to 770 kg of N/ha (converted to the container surface area) was markedly above the fertilizer quantity conventionally employed under practice conditions, so that the tolerance limit was exceeded in some of the standard fertilizers such as urea or ammonium nitrate, which were employed for comparison, and plant damage was provoked.

The examples which follow illustrate advantages of the invention. Examples 1 to 5 are comparative examples; Examples 6 to 9 are embodiments of the invention. Example 1 is an experiment without added fertilizer; Examples 2 and 3 are experiments with fertilizers without slow-release action. Examples 4 and 5 were carried out with commercially available slow-release fertilizers. In Examples 6 to 8, 3 slow-release fertilizers of the invention were employed. In Example 9 a 1:1 mixture of malonic acid diureide and ammonium nitrate was used. While, in Examples 4 and 5, the action was markedly reduced after only 2 to 3 months, Examples 6 to 8 demonstrated a very uniform nitrogen supply and nitrogen uptake and no plant damage over a period of up to more than 8 months. Example 9 showed a more pronounced initial action combined with an equally good tolerance.

The dry-matter production and nitrogen uptake, respectively, shown in Tables 1 and 2 reveal a noteworthy growth promotion only up to about day 100 after addition in the case of the comparative examples, while a clear nitrogen uptake, and thus dry-matter production, is found up to day 125 and—if measurements were carried out—up to day 252 in the case of the examples of the invention. Thus, the substances employed in accordance with the invention act as slow-release fertilizers with a duration of action of approximately 6 to 9 months.

TABLE 1

| Example No. | Fertilizer | Dry-matter production in g/container, days post-fertilization Days | | | | | | | | | | | |
|---|---|---|---|---|---|---|---|---|---|---|---|---|
| | | 16 | 30 | 45 | 58 | 68 | 78 | 100 | 112 | 125 | 154 | 174 | 252 |
| 1 | — | 3.7 | 0.8 | 0.3 | 0.2 | — | 0.2 | 0.4 | — | 0.6 | — | 1.5 | 0.8 |
| 2 | Urea | 7.7 | 5.6 | 8.6 | 8.6 | — | 5.9 | 2.3 | — | 1.4 | — | 1.4 | — |
| 3 | $NH_4NO_3$ | 8.7 | 8.5 | 11 | 9.1 | — | 7.9 | 2.7 | — | 1.8 | 1 | 0.3 | — |
| 4 | *Ureaform | 9.6 | 3.9 | 2.6 | 1.5 | — | 2.4 | 2.8 | — | 3 | 1.4 | 0.4 | — |
| 5 | **Isodur | 10.2 | 8.1 | 8.8 | 6.4 | — | 3.2 | 1.7 | — | 1.5 | — | 1 | — |
| 6 | Compound IA | 5.7 | 2.5 | 3.8 | 3.1 | — | 5.4 | 6.3 | — | 9.3 | — | 7.2 | 4.5 |
| 7 | Compound IB | 4 | 1.7 | 1.3 | 2.2 | — | 4.6 | — | — | 9.6 | — | — | — |
| 8 | Compound IC | 4.2 | 1.9 | 2.1 | 3.4 | — | 3.3 | — | — | 5.1 | — | — | — |
| 9 | Compound IA + $NH_4NO_3$ 1:1 | — | 14.3 | — | — | 12.6 | — | — | 6.9 | — | — | — | — |

*Urea/formaldehyde condensate, technical-grade product
**Urea/isobutyraldehyde condensate, technical-grade product
IA: R = H, x = —$CH_2$—
IB: R = H, x = —$CH_2CH_2$—
IC: R = H, x = —CH=CH— (trans) or trans —CH=CH—

TABLE 2

| Example | Nitrogen uptake in mg/container; days post-fertilization Days | | | | | | | | | | | | Remarks |
|---|---|---|---|---|---|---|---|---|---|---|---|---|---|
| | 16 | 30 | 45 | 58 | 68 | 78 | 100 | 112 | 125 | 154 | 174 | 252 | |
| 1 | 81 | 17 | 5 | 6 | 0 | 6 | 8 | — | 15 | — | 42 | 25 | — |
| 2 | 480 | 311 | 404 | 410 | — | 127 | 50 | — | 33 | — | 27 | — | Plant damage |
| 3 | 508 | 443 | 523 | 435 | — | 194 | 57 | — | 43 | 21 | 6 | — | Plant damage |
| 4 | 426 | 117 | 76 | 49 | — | 73 | 76 | — | 78 | 33 | 10 | — | — |
| 5 | 529 | 397 | 372 | 234 | — | 76 | 41 | — | 36 | — | 17 | — | Plant damage |
| 6 | 185 | 97 | 130 | 119 | — | 180 | 204 | — | 283 | — | 154 | 145 | — |
| 7 | 114 | 50 | 36 | 69 | — | 161 | — | — | 281 | — | — | — | — |
| 8 | 112 | 60 | 69 | 108 | — | 104 | — | — | 138 | — | — | — | — |
| 9 | — | 671 | — | — | 379 | — | — | 151 | — | — | — | — | — |

EXAMPLE I

Preparation of bis(N'-potassium sulfamate)malonic acid diureide 51 g (0.5 mol) of malonic diamide were dried in vacuo at 70° C. for 30 minutes, suspended in 100 ml of absolute acetonitrile (dried over molecular sieve) and cooled to (−10° C.), 149 g (1.05 mol) of chlorosulfonyl isocyanate were added dropwise at a temperature between (−3) and (−10° C.), and stirring was continued for 2 hours at room temperature. The white crystal slurry was poured onto 2 kg of ice, 138.2 g (1 mol) of potassium carbonate as concentrated solution in water were added, and the resulting white precipitate was filtered off with suction, washed with 0.5 l of water and then 0.5 l of acetone, and dried. This gave 157 g (74%) of bis(N'-potassium sulfamate)malonic acid diureide; decomposition point: 210° C., white powder.

Preparation of bis(N'-potassium sulfamate)succinic diureide 5 g (43 mmol) of succinic diamide were dried in vacuo at 70° C. for 30 minutes, suspended in 100 ml of absolute acetonitrile (dried over molecular sieve) and cooled to (−10° C.), 12.4 g (88 mmol) of chlorosulfonyl isocyanate were added dropwise at a temperature between (−3) and (−10° C.), and stirring was continued for 2 hours at room temperature. The white crystal slurry was poured onto approx. 2 kg of ice, 12.2 g (88 mmol) of potassium carbonate were added as concentrated solution in water, and the resulting white precipitate was filtered off with suction, washed with 0.5 l of water and then with 0.5 l of acetone and dried. This gave 117 g (62%) of bis(N'-potassium sulfamate)succinic diureide; melting point: 250° C., white powder.

To demonstrate the gradual mineralization of the new compounds and thus the liberation of the nutrients which they comprise, the following studies were carried out. The good plant tolerance, even at high application rates, was studied in crop production experiments. To this end, experiments were set up with mustard seedlings as test crop, batches of 20 mustard seeds (Sinapis alba, 'Maxi') being sown into small plastic pots with a capacity of 660 g Limburgerhof soil (humus soil occurring at Limburgerhof). Before sowing, the individual pots were fertilized with increasing amounts of the nitrogenous test substance. During the experiment, the soil was moistened daily to 60% of its maximum water capacity by means of weighing. The experimental parameters recorded were the germination behavior and, over the course of growth, scores for vitality, the extent of N deficiency symptoms ("greenness") and phytotoxicity. A mustard experiment on plant tolerance was terminated after 20 to 30 days, depending on the growth conditions. If necessary, the plant material was additionally weighed to quantitatively determine gradual differences between the treatments. The comparative examples carried out were analogous experiments without nitrogen, with urea as immediately available nitrogen fertilizer and with Isodur®, a commercially available slow-release fertilizer. It can be seen, when the highest application rate of 400 mg N/container is applied, the substances of the invention outperform those of the comparison substances, in particular in the case of the parameters vitality and fresh weight yield (FW yield).

The results are shown in Table 3.

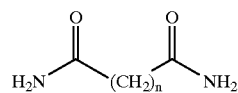

(II)

in which n is 1, 2, 3 or 4 are reacted with chlorosulfonyl isocyanate of the formula (III)

TABLE 3

Effect of urea and various slow-release fertilizers on growth and yield of mustard (seedling test)

| | N content (%) | N fertili- zation [mg/ container] | Vitality (%) 100% optimal growth 0% no growth | | FW yield [g/ container] | "Greenness" (%) (N supply) 100% = dark green | | N content in the DM (%) | N uptake in the shoot [mg/ container] |
|---|---|---|---|---|---|---|---|---|---|
| | | | DAT 9 | DAT 13 | DAT 23 | DAT 13 | DAT 23 | DAT 23 | DAT 23 |
| Without N | | 0 | 95 | 50 | 8.7 | 30 | 30 | 1.8 | 23 |
| Urea | 46 | 100 | 80 | 75 | 19.6 | 100 | 100 | 4.3 | 84 |
| | | 200 | 1 | 1 | 1.6 | 100 | 100 | 6.5 | 10 |
| | | 400 | 0 | 0 | | No growth | due to | unduly high | fertiliza- tion |
| Isodur, ground | 32 | 100 | 100 | 85 | 22.8 | 100 | 100 | 3.8 | 94 |
| | | 200 | 90 | 55 | 20.0 | 100 | 100 | 6.5 | 101 |
| | | 400 | 2 | 1 | 0.2 | 100 | 100 | 6.7 | 2 |
| Succinic diureide bis(potassium sulfonate) (IaA) | 10,5 | 100 | 100 | 50 | 10.4 | 30 | 30 | 1.5 | 27 |
| | | 200 | 100 | 50 | 10.4 | 30 | 30 | 1.7 | 28 |
| | | 400 | 100 | 50 | 10.6 | 30 | 30 | 1.9 | 29 |
| Malonic acid diureide bis(potassium sulfonate) (IaB) | 12 | 100 | 90 | 40+ | 7.1 | 70 | 30 | 3.1 | 46 |
| | | 200 | 60 | 30+ | 4.7 | 80 | 85 | 5.3 | 80 |
| | | 400 | 45 | 20+ | 3.7 | 85 | 85 | 6.6 | 90 |

+= stunted growth, leaves dark green
IaA: R = SO$_2$O$^\ominus$K$^\oplus$, n = 1
IaB: R = SO$_2$O$^\ominus$K$^\oplus$, n = 2

We claim:
1. A diureide of the formula (Ia)

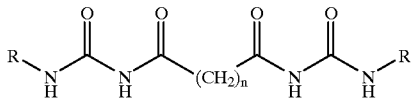

(Ia)

in which

R is SO$_2$O$^\ominus$M$^\oplus$,

M$^\ominus$ is lithium, sodium, potassium, cesium, ammonium, copper, silver, 0.5 iron, 0.5 calcium, 0.5 magnesium, 0.5 manganese, 0.5 zinc or 0.5 cobalt and n is 1,2, 3 or 4.

2. A diureide (Ia) as claimed in claim 1, wherein M$^\oplus$ is lithium, sodium, potassium, cesium or ammonium.

3. A diureide (Ia) as claimed in claim 1, wherein n is 1 or 2.

4. A diureide (Ia) as claimed in claim 1, wherein M$^\oplus$ is sodium or potassium.

5. A diureide (Ia) as claimed in claim 1, wherein M$^\oplus$ is potassium.

6. A process for the preparation of a diureide (Ia) as claimed in claim 1, wherein carboxylic diamides of the formula (II)

at a temperature of −20 to +20° C. and then an aqueous M$_2$CO$_3$ solution, where M is lithium, sodium, potassium, cesium, ammonium, copper, silver, 0.5 iron, 0.5 calcium, 0.5 magnesium, 0.5 manganese, 0.5 zinc or 0.5 cobalt, is added at a temperature of −10 to 0° C. as a further reactant to give the final product of formula (Ia).

* * * * *

UNITED STATES PATENT AND TRADEMARK OFFICE
CERTIFICATE OF CORRECTION

PATENT NO. : 6,353,134 B1  
DATED : March 5, 2002  
INVENTOR(S) : Von Locquenghien et al.

Page 1 of 1

It is certified that error appears in the above-identified patent and that said Letters Patent is hereby corrected as shown below:

<u>Title page,</u>  
ABSTRACT  
Lines 5 and 17, "$SO_2OM^{\oplus}$" should be -- $SO_2O^{\ominus}M^{\oplus}$ --  
Line 18, "M is lithium" should be -- $M^{\oplus}$ is lithium --.

<u>Column 7,</u>  
Line 53, "$M^{\ominus}$" should be -- $M^{\oplus}$ --.

Signed and Sealed this

Fourteenth Day of May, 2002

Attest:

Attesting Officer

JAMES E. ROGAN  
*Director of the United States Patent and Trademark Office*